US007638296B1

(12) United States Patent
Carcagno et al.

(10) Patent No.: US 7,638,296 B1
(45) Date of Patent: Dec. 29, 2009

(54) METHOD FOR THE MASSIVE CULTURE OF CELLS PRODUCING RECOMBINANT HUMAN ERYTHROPOIETIN

(75) Inventors: Carlos Miguel Carcagno, Capital Federal (AR); Marcelo Eduardo Criscuolo, Capital Federal (AR); Carlos Alberto Melo, Buenos Aires (AR); Miguel Alejandro Vidal, Buenos Aires (AR)

(73) Assignee: Sterrenbeld Biotechnologie North America, Inc., Wilmington, DE (US)

( * ) Notice: Subject to any disclaimer, the term of this patent is extended or adjusted under 35 U.S.C. 154(b) by 0 days.

(21) Appl. No.: 09/830,968

(22) PCT Filed: Nov. 8, 1999

(86) PCT No.: PCT/US99/26240

§ 371 (c)(1),
(2), (4) Date: Nov. 6, 2001

(87) PCT Pub. No.: WO00/27997

PCT Pub. Date: May 18, 2000

(30) Foreign Application Priority Data

Nov. 6, 1998  (AR) ............................. P980105611
Feb. 23, 1999 (AR) ............................. P990100681

(51) Int. Cl.
*C12P 21/06* (2006.01)
(52) U.S. Cl. ...................... 435/69.1; 435/325; 435/455
(58) Field of Classification Search ............... 435/69.1, 435/69.6, 320.1, 455, 325, 358; 210/637, 210/649; 530/350
See application file for complete search history.

(56) References Cited

U.S. PATENT DOCUMENTS

| 3,865,801 A | * | 2/1975 | Chiba et al. ................. 530/397 |
| 4,667,016 A | | 5/1987 | Lai et al. ..................... 530/397 |
| 4,677,195 A | | 6/1987 | Hewick et al. ............. 530/397 |
| 4,703,008 A | | 10/1987 | Lin ........................... 435/240.2 |
| 4,806,524 A | | 2/1989 | Kawaguchi et al. ............. 514/8 |
| 5,010,002 A | | 4/1991 | Levinson et al. ........... 435/69.2 |
| 5,490,937 A | * | 2/1996 | van Reis ...................... 210/637 |
| 5,547,933 A | | 8/1996 | Lin ................................ 514/8 |
| 5,618,698 A | | 4/1997 | Lin ............................. 435/69.4 |
| 5,688,679 A | | 11/1997 | Powell ..................... 435/240.2 |
| 5,756,349 A | | 5/1998 | Lin ............................. 435/325 |
| 5,783,559 A | | 7/1998 | Florin-Robertsson et al. . 514/12 |

FOREIGN PATENT DOCUMENTS

| EP | 0513738 A2 * | 5/1992 |
| JP | 05/252942 A | 5/1993 |
| WO | WO 86/03520 | 6/1986 |
| WO | WO 98/00530 | 1/1998 |
| WO | WO 00/27419 | 5/2000 |
| WO | WO 00/27869 | 5/2000 |
| WO | WO 00/27997 | 5/2000 |
| WO | WO 00/28066 | 5/2000 |

OTHER PUBLICATIONS

Jixian et al, Bull Acad. Mil. Med. Sci. 21(4):244-246, 1997 English translation.*
Yanagi et al, DNA 8(6):419-427, 1989.*
GIBCO BRL Procucts and Referecnce Guide, Cell culture sec. 1-10, 25, 39, 63. 1997-1998.*
Wang et al Biotechnol Bioeng. 77(2):194-203. 2002.*
Yang et al, Biotechnol Prog. 18(1):129-38., 2002.*
Schroder et al J Biotechnol. 108(3):279-92, 2004.*
Andersen, D.C. and Goochee, C.F., "The effect of cell-culture conditions on the oligosaccharide structures of secreted glycoprotein," *Curr. Op. Biotech.* 5:546-549, Current Biology Ltd. (1994).
Bondurant, M.C. and Koury, M.J., "Anemia Induces Accumulation of Erythropoietin mRNA in the Kidney and Liver," *Mol. Cell. Biol.* 6:2731-3, American Society for Microbiology (1986).
Borsook, H., et al., "Polycythemic Response in Normal Adult Rats to a Nonprotein Plasma Extract from Anemic Rabbits," *Blood* 9:734-742, Grune and Stratton, Inc. (1954).
Bowie, J.U., et al., "Deciphering the Message in Protein Sequences: Tolerance to Amino Acid Substitutions," *Science* 247:1306-1310, American Association for the Advancement of Science (1990).
Brown, P.R. and Krstulovic, A.M., "Practical Aspects of Reverse-Phase Liquid Chromatography Applied to Biochemical and Biomedical Research," *Anal. Biochem.* 99:1-21, Academic Press, Inc. (1979).
Burg, J., et al., "Human erythropoietin recombinant production by fermentation and protein purification using a series of chromatographic steps," *Chem. Abstracts* 126:315 Abstract No. 57095j, American Chemical Society (1997).
Busuttil, R.W., et al., "The Cytological Localization of Erythropietin in the Human Kidney Using the Fluorescent Antibody Technique," *Proc. Soc. Exp. Biol. Med.* 137:327-330, Academic Press, Inc. (1971).
Busuttil, R.W., et al., "Localization of Erythropoietin in the Glomerulus of the Hypoxic Dog Kidney Using a Fluorescent Antibody Technique," *Acta Haemat.* 47:238-242, S. Karger (1972).
Caro, J. and Erslev, A.J., "Biologic and immunologic erythropoietin in extracts from hypoxic whole rat kidneys and in their glomerular and tubular fractions," *J. Lab. Clin. Med* 103:922-931, C.V. Mosby Company (1984).

(Continued)

*Primary Examiner*—Michael C. Wilson
(74) *Attorney, Agent, or Firm*—Sterne, Kessler, Goldstein & Fox P.L.L.C.

(57) ABSTRACT

The present invention relates, in general, to a method for the massive culture of recombinant mammalian cells for the production of recombinant human erythropoietin (EPO) in culture medium containing insulin. The present invention also refers to a method of producing EPO and to the EPO thus produced.

13 Claims, 4 Drawing Sheets

OTHER PUBLICATIONS

Caro, J., et al., "Erythropoietin Production by an Established Kidney Proximal Tubule Cell Line (LLCPK$_1$)," *Exp. Hematol* 12:357, Springer-Verlag (1984).

Caro, J., et al., "Erythropoietin in liver tissue extracts and in liver perfusates from hypoxic rats," *Am. J. Physiol.* 244:E431-E434, American Physiological Society (1983).

Dinkelaar, R.B., et al., "Metabolic Studies on Erythropoietin (Ep): II. The Role of Liver and Kidney in the Metabolism of Ep," *Exp. Hematol.* 9:796-803, Allen Press, Inc. (1981).

Dornfest, B.S., et al., "Hepatic production of erythropoietin in a phenylhydrazine-induced compensated hemolytic state in the rat," *J. Lab. Clin. Med.* 102:274-85, C.V. Mosby Company (1983).

Dornfest, B.S., et al., "Recovery of an Erythropoietic Inducing Factor from the Regenerating Rat Liver," *Ann. Clin. Lab. Sci.* 11:37-46, Institute for Clinical Science (1981).

Erslev, A., "Humoral Regulation of Red Cell Production," *Blood* 8:349-357, Grune and Stratton, Inc. (1953).

Erslev, A.J., "In Vitro Production of Erythropoietin by Kidneys Perfused With a Serum-free Solution," *Blood* 44:77-85, Grune and Stratton, Inc. (1974).

Erslev, A.J. and Caro, J., "Physiologic and Molecular Biology of Erythropoietin," *Med. Oncol. Tumor Pharmacother.* 3:159-164, Pergamon Press (1986).

Eschbach, J.W., et al., "Correction of the Anemia of End-Stage Renal Disease with Recombinant Human Erythropoietin," *New Eng. J. Med.* 316:73-78, Massachusetts Medical Society (1987).

Fisher, J.W. and Birdwell, B.J., "The Production of an Erythropoietic Factor by the In Situ Perfused Kidney," *Acta. Haemat.* 26:224-232, S. Karger (1961).

Fisher, J.W., et al., "Localization of Erythropoietin in Glomeruli of Sheep Kidney by Fluorescent Antibody Technique," *Nature* 205:611-612, Macmillan Magazines Ltd. (1965).

Fisher, J.W., "Pharmacologic Modulation of Erythropoietin Production," *Ann. Rev. Pharmacol. Toxicol.* 28:101-122, Annual Reviews, Inc. (1988).

Frenkel, E.P., et al., "Some Observations on the Localization of Erythropoietin," *Ann. N.Y. Acad. Sci.* 149:292-293, New York Academy of Sciences (1968).

Gordon, A.S., et al., "A Plasma Extract with Erythropoietic Activity," *Proc. Soc. Exp. Biol. Med.* 86:255-258, Society for Experimental Biology and Medicine (1954).

Han, F., et al., "Cloning of a human erythropoietin cDNA and its expression in COS-7 cells," *Chem. Abstracts* Abstract No. 511352 (1996).

Hodgson, G. and Tohá, J., "The Erythropoietic Effect of Urine and Plasma of Repeatedly Bled Rabbits," *Blood* 9:299-309, Grune and Stratton, Inc. (1954).

Jacobs, K., et al., "Isolation and characterization of genomic and cDNA clones of human erythropoietin," *Nature* 313:806-810, Macmillan Magazines Ltd. (1985).

Jacobson, L.O., et al., "Role of the Kidney in Erythropoiesis," *Nature* 179:633-634, Macmillan Magazines Ltd. (1957).

Jelkmann, W., et al., "Extraction of Erythropoietin from Isolated Renal Glomeruli of Hypoxic Rats," *Exp. Hematol.* 11:581-588, Allen Press, Inc. (1983).

Jixian, D., et al., "Study on a serum-free medium used for production of rHuEPO," *Bull. Acad. Mil. Med. Sci.* 21:244-246, Academy of Military Medical Sciences (1997).

Kazal, L.A. and Erslev, A.J., "Erythropoietin Production in Renal Tumors," *Ann. Clin. Lab. Sci.* 5:98-109, Institute for Clinical Science (1975).

Krane, N.K., "The Role of Erythropoietin in the Anemia of Chronic Renal Failure," *H. Ford Hosp. Med. J.* 31:177-181, Henry Ford Hospital (1983).

Koury, S.T., et al., "Localization of Erythropoietin Synthesizing Cells in Murine Kidneys by In Situ Hybridization," *Blood* 71:524-527, Grune and Stratton, Inc. (1988).

Koury, S.T., et al., "Quantitation of Erythropoietin-Producing Cells in Kidneys of Mice by In Situ Hybridization: Correlation With Hematocrit, Renal Erythropoietin mRNA, and Serum Erythropoietin Concentration," *Blood* 74:645-651, Grune and Stratton, Inc. (1989).

Kuratowska, Z., et al., "Studies on the Production of Erythropoietin by Isolated Perfused Organs," *Blood* 18:527-534, Grune and Stratton, Inc. (1961).

Kurtz, A., et al., "Renal mesangial cell cultures as a model for study of erythropoietin production," *Proc. Natl. Acad. Sci. USA* 80:4008-4011, National Academy of Sciences (1983).

Lacombe, C., et al., "Peritubular Cells Are the Site of Erythropoietin Synthesis in the Murine Hypoxic Kidney," *J. Clin. Invest.* 81:620-623, Rockefeller University Press (1988).

Liu, P., et al., "Hepatic Erythropoietin (Ep) Production Following Double Partial Hepatectomy in the Rat," *J. Surg. Oncol.* 15:121-132, Alan R. Liss, Inc. (1980).

Naughton, B.A., et al., "Reticuloendothelial System (RES) Hyperfunction and Erythropoietin (Ep) Production in the Regenerating Liver," *J. Surg. Oncol.* 12:227-242, Alan R. Liss, Inc.(1979).

Naughton, B.A., et al., "Evidence for a Hepatic-Renal Antagonism in the Production of Hepatic Erythropoietin," *Ann. Clin. Lab. Sci.* 13:432-438, Institute for Clinical Science (1983).

Parsons, T.F., et al., "Rapid and Easy Separation of the Subunits of Bovine and Human Glycoprotein Hormones by Use of High Performance Liquid Chromatography," *Endocrinology* 114: 2223-2227, J.B. Lippincott Co. (1984).

Reisman, K.R., "Studies on the Mechanism of Erythropoietic Stimulation in Parabiotic Rats During Hypoxia," *Blood* 5:372-380, Grune and Stratton, Inc. (1950).

Schuster, J.H., et al., "Physiologic Regulation and Tissue Localization of Renal Erythropoietin Messenger RNA," *Blood* 70:316-318, Grune and Stratton, Inc.(1987).

Sherwood, J.B., et al., "Erythropoietin Production by Human Renal Carcinoma Cells in Culture," *Endocrinology* 99:504-510, J.B. Lippincott Co. (1976).

Takagaki, Y., et al., "Amino Acid Sequence of the Membranous Segment of Rabbit Liver Cytochrome $b_5$," *J. Biol. Chem.* 255:1536-1541, American Society of Biological Chemists, Inc. (1980).

Werber, M.M., et al., "Preliminary purification of two human blood cell hormones by hydrophobic interaction chromatography," *Chem. Abstracts* 100:77 Abstract No. 203779s, American Chemical Society (1984).

Pending Non-Provisional U.S. Appl. No. 09/830,967, Carcagno et al., filed May 3, 2001.

Pending Non-Provisional U.S. Appl. No. 09/830,964, Carcagno et al., filed May 3, 2001.

International Search Report of International Application No. PCT/US99/26238, Mar. 7, 2000.

International Search Report of International Application No. PCT/US99/26241, Mar. 7, 2000.

International Search Report of International Application No. PCT/US99/26240, Feb. 22, 2000.

International Search Report of International Application No. PCT/US99/26237, Feb. 18, 2000.

Lee, G.M., et al., "Development of a serum-free medium for the production of erythropoietin by suspension culture of recombinant Chinese hamster ovary cells using a statistical design," *J. Biotechnol.* 69:85-93, Elsevier (Apr. 1999).

Supplementary European Search Report for European Patent Application No. EP 99 95 8810, mailed Mar. 16, 2005, European Patent Office, Rijswijk, Netherlands.

Derwent World Patents Index, English language abstract for Chinese Patent No. CN 1190130, Accession No. 2003-175924.

Derwent World Patents Index, Dialog File 351, English language abstract for European Patent No. EP 0 513 738, Accession No. 9256229.

Hu, Y., et al., "An improved, inexpensive procedure for the large-scale purification of recombinant human erythropoietin," *Biotechnol. Appl. Biochem.* 40:89-94, Portland Press Ltd. (Aug. 2004).

* cited by examiner

METHOD FOR THE MASSIVE CULTURE OF CELLS PRODUCING RECOMBINANT HUMAN ERYTHROPOIETIN

This Application claims benefit under 35 U.S.C. § 371 of International Application No. PCT/US99/26240, filed on 8 Nov. 1999, which was published under PCT Article 21(2) in English and which is fully incorporated herein by reference.

BACKGROUND OF THE INVENTION

1. Field of the Invention

The present invention relates, in general, to a method for the massive culture of recombinant mammalian cells for the production of recombinant human erythropoietin (EPO) in a culture medium containing insulin. The present invention also refers to a method of producing EPO and to the EPO thus produced.

2. Background Information

EPO is a glycoprotein that stimulates erythroblast differentiation in the bone marrow, thus increasing the circulating blood erythrocyte count. The mean life of erythrocytes in humans is 120 days and therefore, a human being loses 1/120 erythrocytes each day. This loss must be continuously restored to maintain an adequate level of red blood cells.

The existence of EPO was first postulated by the turn of the century and was definitely proved by Reissman and Erslev early in the '50s. See Carnot, et al., *C.R. Acad. Sci.* (France), 143, 384-6 (1906); Carnot, et al., *C.R. Acad. Sci.* (France), 143, 432-5 (1906); Carnot, et al., *C.R. Soc. Biol.*, 111, 344-6 (1906); Carnot, *C.R. Soc. Biol.*, 111, 463-5 (1906); Reissman, *Blood,* 1950, 5, 372-80 (1950) and Erslev, *Blood,* 8, 349-57 (1953). Reissman and Erslev's experiments were promptly confirmed by other researchers. See Hodgson, et al., *Blood,* 9, 299-309(1954); Gordon, et al., *Proc. Soc. Exp. Biol. Med.,* 86, 255-8 (1954) and Borsook, et al., *Blood,* 9, 734-42 (1954).

The identification of the EPO production site in the organism was an issue of debate. Successive experiments led to identify the kidney as the main organ and peritubular interstitial cells as the synthesis site. See Jacobson, et al., *Nature,* 179, 633-4 (1957); Kuratowska, et al., *Blood,* 18, 527-34 (1961); Fisher, *Acta Hematol.,* 26, 224-32 (1961); Fisher, et al., *Nature,* 205, 611-2 (1965); Frenkel, et al., *Ann. N.Y. Acad. Sci.,* 149, 1, 292-3 (1968); Busuttil, et al., *Proc. Soc. Exp. Biol. Med.,* 137, 1, 327-30 (1971); Busuttil, *Acta Haematol.,* (Switzerland), 47, 4, 238-42 (1972); Erslev, *Blood,* 44, 1, 77-85 (1974); Kazal, *Ann. Clin. Lab. Sci.,* 5, 2, 98-109 (1975); Sherwood, et al., *Endocrinology,* 99, 2, 504-10 (1976); Fisher, *Ann. Rev. Pharmacol. Toxicol.,* 28, 101-22 (1988); Jelkmann, et al., *Exp. Hematol.,* 11, 7, 581-8 (1983); Kurtz, et al., *Proc. Natl. Acad. Sci.* (USA), 80, 13, 4008-11 (1983); Caro, et al., *J. Lab. Clin. Med.,* 103, 6, 922-31 (1984); Caro, et al., *Exp. Hematol.,* 12, 357 (1984); Schuster, et al., *Blood,* 70, 1, 316-8 (1986); Bondurant, et al., *Mol. Cell. Biol.,* 6, 7, 2731-3 (1986); Bondurant, et al., *Mol. Cell. Biol.,* 6, 7, 2731-3 (1986); Schuster, et al., *Blood,* 71, 2, 524-7 (1988); Koury, et al., *Blood,* 71, 2, 524-7 (1988); Lacombe, et al., *J. Clin. Invest.,* 81, 2, 620-3 (1988); Koury, et al., *Blood,* 74, 2, 645-51 (1989).

A smaller proportion, ranging from 10% to 15% of total EPO, is produced by the liver in adults. See Naughton, et al., *J. Surg. Oncol.,* 12, 3, 227-42 (1979); Liu, et al., *J. Surg. Oncol.,* 15, 2, 121-32 (1980); Dornfest, et al., *Ann. Clin. Lab. Sci.,* 11, 1, 37-46 (1981); Dinkelaar, et al., *Exp. Hematol.,* 9, 7, 796-803 (1981); Caro, et al., *Am. J. Physiol.,* 244, 5 (1983); Dornfest, et al., *J. Lab. Clin. Med.,* 102, 2, 274-85 (1983); Naughton, et al., *Ann. Clin. Lab. Sci.,* 13, 5, 432-8 (1983); Jacobs, et al., *Nature,* 313, 6005, 806-10 (1985); Erslev, et al., *Med. Oncol. Tumor. Pharmacother.,* 3, 3-4, 159-64 (1986). The EPO produced is directly proportional to the extent of tissular hypoxia and its expression rises by increasing the number of the EPO producing cells.

EPO has shown great efficiency in the treatment of anemia, especially anemia derived from renal failure. See Eschbach, et al., *N. England J. of Med.,* 316, 2, 73-78 (1987); Krane, *Henry Ford Hosp. Med. J,* 31, 3, 177-181 (1983). Its therapeutical usefulness, however, has been limited due to the unavailability of a massive production method. The quantity and quality of the EPO obtained by the extractive systems known were insufficient. Recently, the use of recombinant DNA technology has made it possible to obtain large amounts of proteins. The application of these techniques to eukaryotic cells has allowed a large scale production of EPO. See U.S. Pat. No. 5,688,679 (to Powell), U.S. Pat. No. 5,547,933 (to Lin), U.S. Pat. No. 5,756,349 (to Lin), U.S. Pat. No. 4,703, 008 (to Lin) and U.S. Pat. No. 4,677,195 (to Hewick et al.)

Notwithstanding the recent considerable literature referring to the production of EPO in mammalian cell cultures, no method has yet been devised to produce efficiently EPO in industrial scale. The existent EPO culture systems are further characterized by their low reproducibility and output quality. See U.S. Pat. No. 5,688,679 (to Powell); U.S. Pat. No. 5,547, 933 (to Lin); U.S. Pat. No. 5,756,349 (to Lin); U.S. Pat. No. 4,703,008 (to Lin) and U.S. Pat. No. 4,677,195 (to Hewick et al.); Andersen, et al., *Curr. Op. Biotech,* 5, 546-549 (1994); Butler, Ed., "Mammalian Cell Biotechnology", (IRL Press, Oxford, England, 1991); Murakami, Ed., "Trends in Animal Cell Culture Technology", (Kodansha Ltd., Tokyo, Japan, 1990); Freshney, Ed., "Animal Cell Culture. A Practical Approach," Ch. 3, (IRL Press, Oxford, England, 1986); Pirt, "Principles of Microbe and Cell Cultivation", (Blackwell Scientific Pub., London, England, 1985); Hames et als., "Transcription and Translation. A Practical Approach", (IRL Press, Oxford, England, 1984).

SUMMARY OF THE INVENTION

The present invention provides a method for obtaining human erythropoietin (EPO) comprising culturing mammalian cells which express recombinant human erythropoietin in a culture medium comprising insulin.

The invention specifically relates to a method for obtaining human EPO that comprises the separation of a supernatant comprising EPO and insulin from cells which express recombinant human EPO, the concentration of said supernatant and the freezing of the resulting concentrated product.

The present invention describes a method for the massive culture of recombinant cells adequate for the industrial production of EPO. The method described in the present invention produces an unexpectedly high amount of EPO with a low concentration of contaminant proteins in the culture medium. This condition enhances the subsequent EPO purification steps and results in a high protein recovery ratio. The high yield of EPO obtained by the claimed method is achieved by the addition of insulin to the culture medium.

Other advantages of the claimed method are: 1) its reproducibility and 2) the high quality of the EPO obtained regardless of the protein production scale.

The method claimed in the present invention utilizes EPO producing cells preserved in liquid nitrogen (Master and Working Bank). The cells are thawed and multiplied through successive expansion steps at 37° C. with different culture media. The expansion is sustained until a cellular mass adequate for industrial scale production is achieved. The cells are grown in T25 (25 cm² surface area) flasks and transferred to flasks with increasing surface areas until a final roller flask surface of 850 cm² is reached. The culture medium employed for the cell expansion is then replaced by an improved culture medium containing insulin to enhance the production of EPO. After 72 hours, the EPO containing supernatant is first recovered, purified and assayed.

The obtained culture supernatant is assayed by SDS-PAGE, Western blot, glycanase treatment followed by SDS-PAGE, isoelectric focusing and a complete protein sequence analysis to verify the identity of the EPO produced. The in vivo biological activity of the EPO thus produced is determined by an ex-hypoxic polycythemic mice assay using the World Health Organization EPO standard as reference.

DETAILED DESCRIPTION OF THE INVENTION

The present invention provides a method for obtaining EPO comprising the culture of mammalian cells which express recombinant human erythropoietin in a substrate medium comprising insulin. The claimed invention is further characterized by the absence of fetal calf serum from the culture medium.

The EPO expressing cells in the present invention are selected from the group comprising mammalian cells. Preferably said mammalian cells are selected from the group comprising CHO, COS, BHK, Namalwa, and HeLa cells, and even more preferably said mammalian cells are CHO cells.

Preferred recombinant host cells comprise a vector which comprises a nucleotide sequence encoding the EPO polypeptide consisting of the amino acid sequence in SEQ ID NO:1, a viral promoter and a viral terminator. Preferred host cell vectors confer resistance to both methotrexate and neomycin-derived antibiotics. Preferably, the EPO nucleic acid molecule comprises the nucleic acid molecule described in Lin, "DNA Sequences Encoding Erythropoietin," U.S. Pat. No. 4,703,008. Preferably, the viral promoter is an SV40 early promoter.

The insulin in the culture medium in the above and below-described methods can be present in amounts from about 0.1 mg per liter of culture medium to about 40 mg per liter of culture media, and even more preferably from about 0.5 mg per liter of culture media to about 20 mg per liter of culture media.

In a further embodiment, the invention provides a method for obtaining human erythropoietin comprising the culture of mammalian cells which express recombinant human erythropoietin in culture media which comprises fetal calf serum-free media.

The invention also provides a method for obtaining EPO by separating the supernatant comprising EPO and insulin from mammalian cells which express recombinant human erythropoietin, concentrating said supernatant and freezing the concentrated product.

The invention provides the above and below-described methods wherein said concentration step concentrates the supernatant from about 25 to 200 fold, preferably about 50 to 150 fold, and most preferably 100 fold.

The invention provides the above and below-described methods wherein said concentration step comprises using a tangential filtration system through membranes with a molecular weight cut-off of about 3,000 Daltons.

The invention also provides a method for obtaining human erythropoietin by separating the supernatant comprising EPO and insulin from mammalian cells which express recombinant human erythropoietin, concentrating said supernatant, freezing the concentrated product and sterile filtering said concentrated product. Preferably said sterile filtering is through membranes with a pore diameter ranging from about 0.1 to about 0.2 μm, and most preferably about 0.2 μm.

The EPO protein can be further purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

A preferred method of further purifying the EPO comprises treating cell culture supernatants comprising EPO by a combination of the following steps: (a) differential precipitation, (b) hydrophobic interaction chromatography, (c) diafiltration, (d) anionic exchange chromatography, (e) cationic exchange chromatography and (f) molecular exclusion chromatography. Preferably, said steps are performed in the following order: (a), (b), (c), (d), (e), and (f).

A preferred method of using the EPO produced by the culturing of the present invention comprises lyophilization into a form suitable for injection into humans for the treatment of diseases. Specifically, the preferred lyophilization procedure comprises placing the EPO into a pharmaceutical composition, loading the first EPO composition into a container, wherein said container is at a temperature equal to or less than −30° C.; incubating said EPO composition at a temperature equal to or less than −30° C. under atmospheric pressure for a time equal to or greater than 4 hours; exposing said composition at a pressure of equal to or less than 30 absolute microns for a time equal to or greater than one hour; and raising the temperature equal to or less than 3° C. per hour until reaching at least 25° C., while keeping pressure values equal to or less than 5 absolute microns.

A preferred pharmaceutical composition for lyophilization comprises EPO, sugar, salts and human albumin. An especially preferred composition for lyophilization comprises EPO, mannitol, NaCl, $NaH_2PO_4$, $Na_2HPO_4$ and human albumin.

The invention also provides a method for obtaining human erythropoietin by separating the supernatant comprising EPO and insulin from mammalian cells which express recombinant human erythropoietin, adding media comprising insulin to separated cells and culturing said cells.

The present invention is described in further detail in the following non-limiting examples.

EXAMPLES

Example 1

Culture

The recombinant human EPO is produced in a mammalian cell line (CHO) transfected with human erythropoietin genomic DNA. The cell banks ("Master" and "Working Bank") containing the EPO producing cells were preserved in liquid nitrogen according to commonly used laboratory methods. See Hames et al., "Transcription and Translation. A Practical Approach", (IRL Press, Oxford, England, 1984), incorporated herein as reference. Four "seeds" from the EPO working bank were thawed and added separately to four T 25 flasks containing 10 ml of culture medium no. 1 each. See Table 1. For each T 25 flask the following protocol was applied:

The EPO producing cells were cultured for 24 hours at 37° C. The culture medium was then removed and 10 ml of medium no. 2 were added to each T 25 flask. See Table 1. The cell cultures were preserved at the same conditions for an additional 24 hour period. The resulting EPO producing cell cultures were then subject to a series of expansion stages as described in the following examples.

Example 2

Expansion 1

Each cell culture from Example 1 was removed from the T 25 flasks by trypsin treatment according to commonly used laboratory methods. See Hames et al., supra. Afterwards, the cell cultures were grown according to the following protocol: to each one of five T 25 flasks, 20% of each grown cell culture and 10 ml of culture medium no. 2 were added. See Table 1. The EPO producing cell cultures were incubated further for 48 hours at 37° C.

Example 3

Expansion 2

The five cell cultures from the previous example were removed from the T 25 flasks by trypsin treatment according to commonly used laboratory methods. See Hames et al., supra. Each cell culture was transferred to a T 150 flask. Subsequently, 75 ml of culture medium no. 1 were added to each T 150 flask. See Table 1. The EPO producing cell cultures were then incubated for 72 hours at 37° C.

Example 4

Expansion 3

The cell cultures from the previous example were removed from the T 150 flasks by trypsin treatment according to commonly used laboratory methods. See Hames et al., supra. 10% of the cell culture of each T 150 flask was transferred to a new T 150 flask. 75 ml of culture medium no. 1 were added to each new T 150 flask. See Table 1. The EPO producing cell cultures were then incubated for 72 hours at 37° C.

Example 5

Expansion 5

The cell cultures from the previous example were removed from the T 150 flasks by trypsin treatment according to commonly used laboratory methods. See Hames et al., supra. The cell cultures from each T 150 flask were transferred to a "roller" flask of 850 $cm^2$ of inner surface. 200 ml of culture medium no. 1 were added to each roller flask. See Table 1. The EPO producing cell cultures were then incubated for 72 hours at 37° C.

Example 6

Expansion 6

The cell cultures from the previous example were removed from the roller flasks by trypsin treatment according to commonly used laboratory methods. See Hames et al., supra. $\frac{1}{15}^{th}$ of each cell culture was transferred to a new roller flask. In total 3,000 roller flasks containing the EPO producing cell culture were prepared and grown according to the following protocol:

200 ml of culture medium no. 1 were added to each roller flask. The EPO producing cell cultures were then incubated for 72 hours at 37° C. The roller rotation speed was 11 rounds per hour.

The formation of a cell monolayer was verified by an inverted microscopic analysis. The culture medium of each roller flask was discarded and the EPO producing cell cultures were rinsed with 300 ml Hank's solution per roller. See Table 1. 200 ml of culture medium no. 3 was then added to each roller flask.

Example 7

Harvest

The culture supernatant of each cell culture from the preceding example was harvested every 48 hours, under strict sterile conditions, and replaced with 200 ml of fresh culture medium no. 3. This procedure was repeated 5 times for each roller flask.

The harvested culture supernatant was concentrated a hundred-fold with a tangential filtration system utilizing 3,000 D cut off Amicon S10Y3 membranes. The concentrated material was filtered under sterile conditions and stored at −20° C.

A cellular density between 180,000 cells per $cm^2$ and 800,000 cell per $cm^2$ was achieved. Cell viablity ranged between 95% and 98% throughout the whole procedure. The harvested supernatant was 2,900 liters. The material concentrated according to example 7 yielded 29.5 liters.

The following table summarizes the results of each harvest stage:

| HARVEST | EPO-RIA (g) | TOTAL PROTEINS (g) |
|---------|-------------|---------------------|
| 1 | 26.55 | 51.33 |
| 2 | 38.05 | 95.87 |
| 3 | 37.76 | 100.0 |
| 4 | 32.45 | 134.8 |
| 5 | 33.04 | 161.7 |
| TOTAL | 167.85 | 543.7 |

Example 8

EPO Assays

The EPO obtained in the previous example was further purified and assayed for identity and biological activity according to the following protocol.

Figure 1:
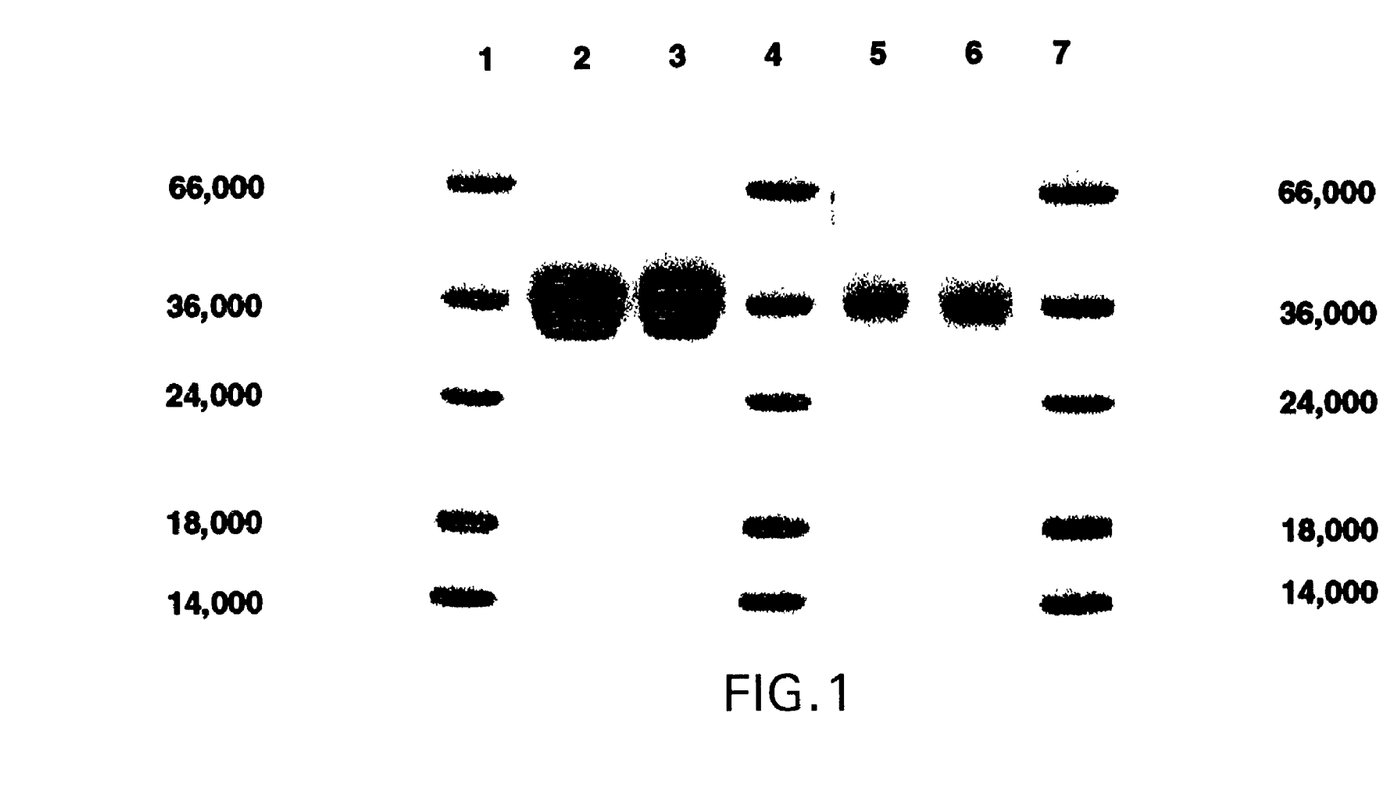
FIG. 1 illustrates a polyacrylamide gel electrophoresis (SDS-PAGE) assay performed on an EPO sample obtained according to the method herein described. Lanes 1, 4 and 7 show molecular weight markers. On lanes 2, 3, 5 and 6 different pure EPO samples were run according to the claimed method. The purity of the obtained product, as well as its apparent molecular weight, somewhat superior to 30 kDa, is coincident with that of urinary human EPO.
Figure 2:
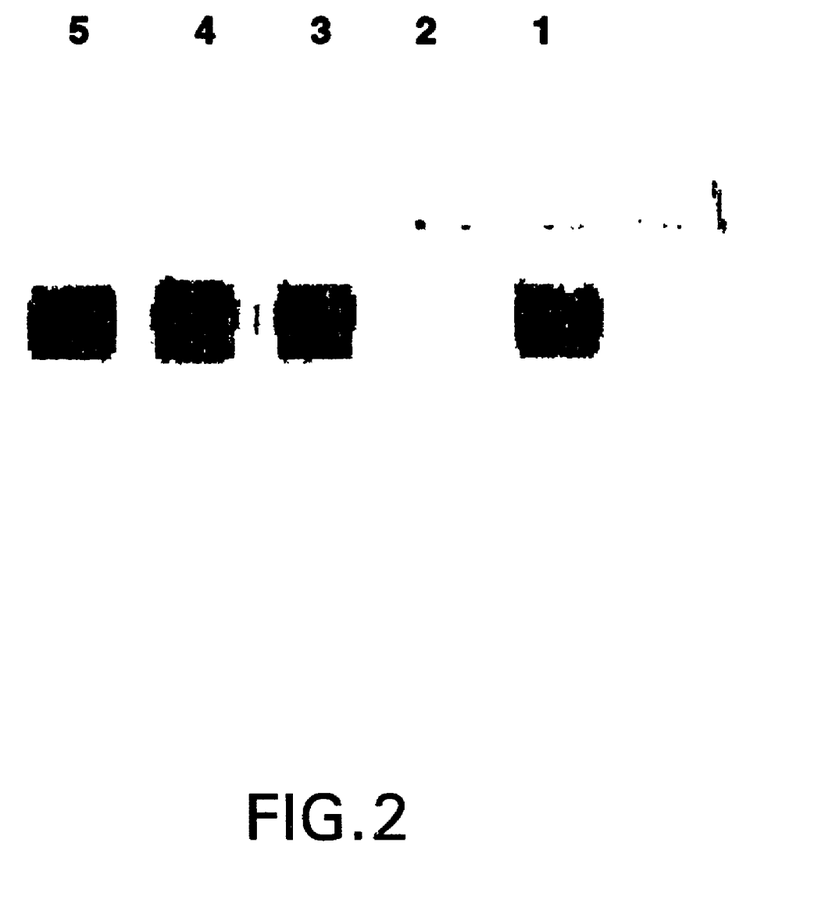
FIG. 2 illustrates a "Western Blot" assay performed on an EPO sample obtained according to the method described herein. The produced EPO identity is verified by the recognition of an antibody against human EPO. On lane 1 a human EPO standard sample was run; on lane 2 molecular weight markers were run and on lanes 3 to 5, EPO samples obtained according to the method claimed herein were run.
Figure 3:
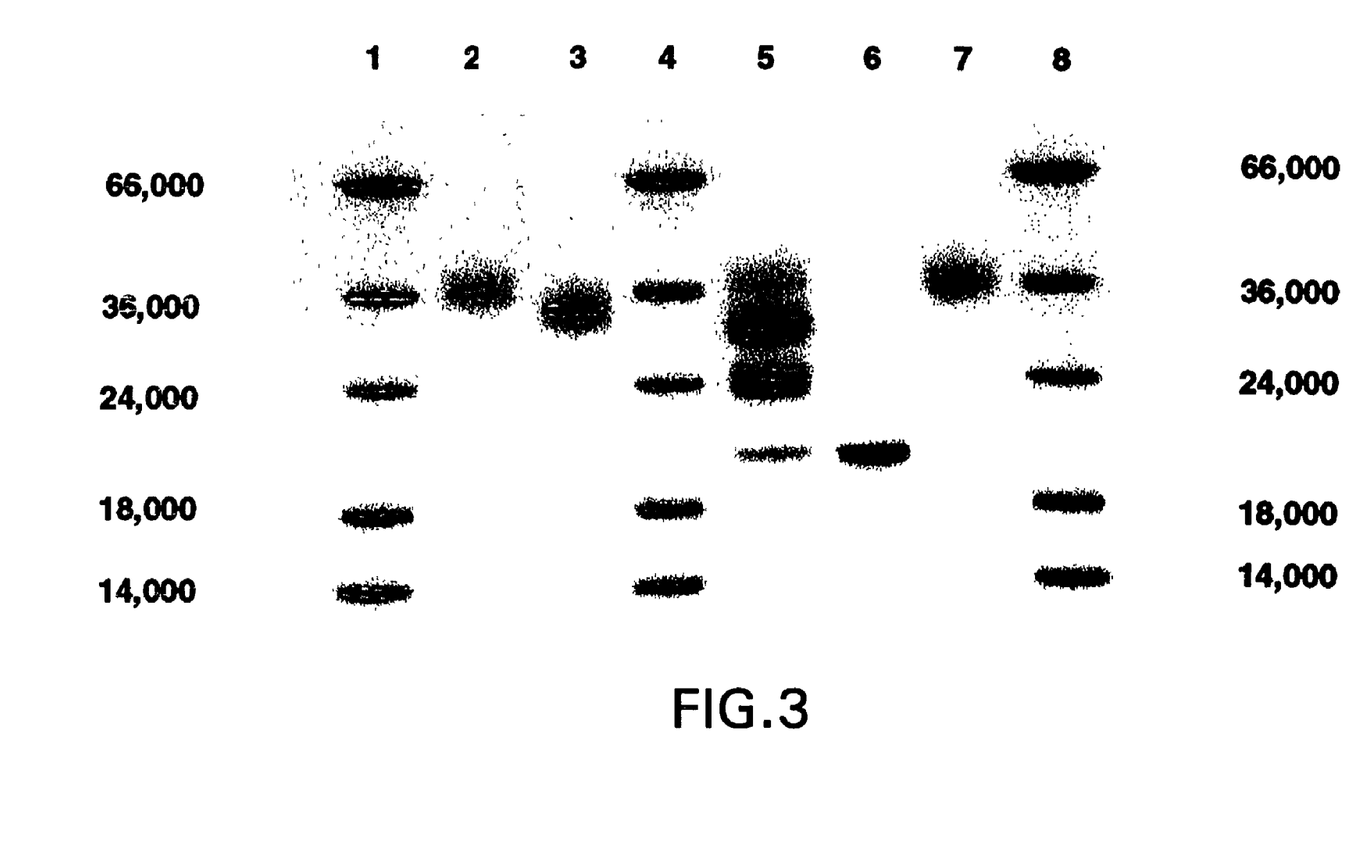
FIG. 3 illustrates a SDS-PAGE assay performed on a pure EPO sample obtained according to the method described herein and submitted to glycanases treatment. Molecular weight markers were run on lanes 1, 4 and 8. Lanes 2 and 7 show untreated EPO samples. On lane 3 an EPO sample treated with O-glycanase was run, showing the existence of an O-glycosilation site. On lane 5 an EPO sample partially degraded with N-glycanase was run, verifying the presence of the molecular weight markers corresponding to those expected for EPO. On lane 6 an EPO sample degraded with O-glycanase and N-glycanase was run, showing the pattern expected for the fully deglycosilated protein.
Figure 4:
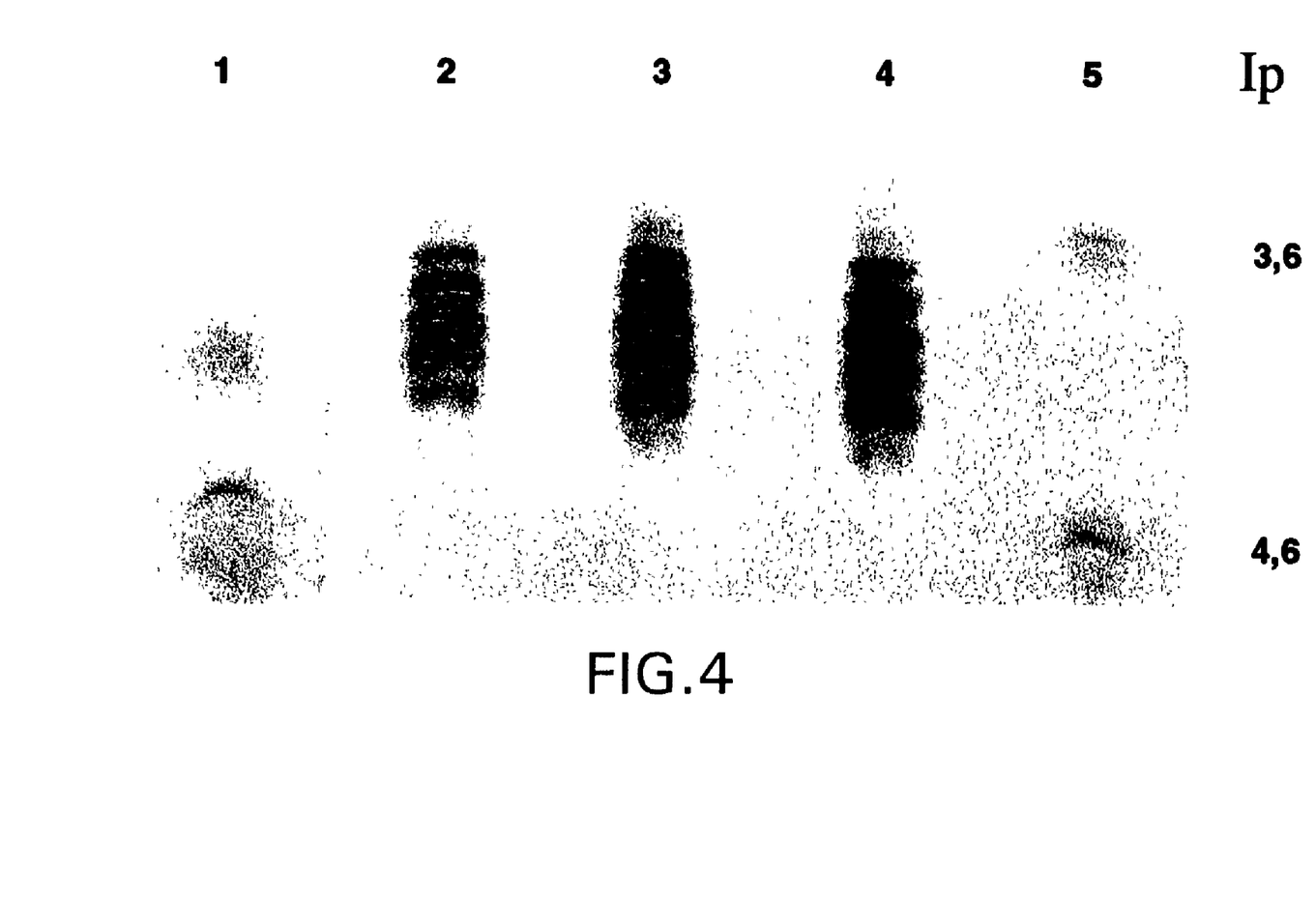
FIG. 4 illustrates an electrofocusing assay performed on pure EPO samples produced according to the method herein described. EPO samples were run on lanes 2, 3 and 4; isoelectric point markers were run on lanes 1 and 5. The presence of the EPO isoforms with isoelectric points ranging from 3.0 to 4.5 is observed.

In a denaturing SDS-PAGE gel EPO was identified as a wide band of molecular weight as expected for EPO. See FIG. 1. The band was recognized by monoclonal and polyclonal antibodies raised against human EPO in a Western blot assay as expected for EPO. See FIG. 2. The treatment with glycanases proved the existence of the glycosidic chains in the extent and size expected for EPO. See FIG. 3. The EPO produced was shown to be composed of a series of species with isoelectric points ranging from 3.0 to 4.5 as expected for EPO. See FIG. 4.

The complete amino acid sequence of the isolated protein, purified from the culture supernatant of transfected cell lines showed total homology with natural human erythropoietin whose 165 amino acid sequence is as follows (SEQ ID NO:1):

| NH$_2$-- | Ala | Pro | Pro | Arg | Leu | Ile | Cys | Asp |
|---|---|---|---|---|---|---|---|---|
| | Ser | Arg | Val | Leu | Glu | Arg | Tyr | Leu |
| | Leu | Glu | Ala | Lys | Glu | Ala | Glu | _Asn_ |
| | Ile | Thr | Thr | Gly | Cys | Ala | Glu | His |
| | Cys | Ser | Leu | Asn | Glu | _Asn_ | Ile | Thr |
| | Val | Pro | Asp | Thr | Lys | Val | Asn | Phe |
| | Tyr | Ala | Trp | Lys | Arg | Met | Glu | Val |
| | Gly | Gln | Gln | Ala | Val | Glu | Val | Trp |
| | Gln | Gly | Leu | Ala | Leu | Leu | Ser | Gln |
| | Ala | Val | Leu | Arg | Gly | Gln | Ala | Leu |
| | Leu | Val | _Asn_ | Ser | Ser | Gln | Pro | Trp |
| | Gln | Pro | Leu | Gln | Leu | His | Val | Asp |
| | Lys | Ala | Val | Ser | Gly | Leu | Arg | Ser |
| | Leu | Thr | Thr | Leu | Leu | Arg | Ala | Leu |
| | Gly | Ala | Gln | Lys | Glu | Ala | Ile | Ser |
| | Pro | Pro | Asp | Ala | Ala | _Ser_ | Ala | Ala |
| | Pro | Leu | Arg | Thr | Ile | Thr | Ala | Asp |
| | Thr | Phe | Arg | Lys | Leu | Phe | Arg | Val |
| | Tyr | Ser | Asn | Phe | Leu | Arg | Gly | Lys |
| | Leu | Lys | Leu | Tyr | Thr | Gly | Gln | Ala |
| | Cys | Arg | Thr | Gly | Asp----COOH | | | |

The presence of the four glycosilation sites on the 165 amino acid chain, as well as the complex carbohydrate structure, and in particular, the sialic acid terminal residues, which characterizes EPO were verified. These results were further supported by a biological activity assay of the produced protein by an ex-hypoxic polycythemic mice test which showed complete concordance with the international EPO standard.

After purification, 30% of the EPO obtained was recovered. The surprisingly high protein yield ratio is attributed to the initial low level of impurities resulting from the claimed invention. The low level of impurities of the culture supernatant is due to the substitution of fetal calf serum by insulin. The insulin substitution prevents the occurrence of metabolites of animal origin in the culture supernatant.

Under the traditional culture methods, which utilize 10% fetal calf serum, the EPO recovery is less than 1%. The recovery ratio of the claimed method is thirty times higher than this.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

Table Number 1

| Culture Medium no. 1 | | | |
|---|---|---|---|
| Basal Culture Medium + 10% Fetal Calf Serum | | | |
| ISCOVE'S DMEM | 8.85 g/l | Tryptophan | 27 mg/l |
| HAM F12 | 5.35 g/l | Asparagine | 40 mg/l |
| NaHCO$_3$ | 2.10 g/l | Serine | 80 mg/l |
| Glucose | 1.30 g/l | Ethanolamine | 3 mg/l |
| Lactose | 0.20 g/l | Glutamine | 1.90 g/l |
| Galactose | 0.20 g/l | Fetal Calf Serum | 100 ml/l |
| Sodium Pyruvate | 0.11 g/l | | |

| Culture Medium no. 2 | | | |
|---|---|---|---|
| Basal Culture Medium + 10% Fetal Calf Serum + Geneticin 0.5 mg/ml | | | |
| ISCOVE'S DMEM | 8.85 g/l | Tryptophan | 27 mg/l |
| HAM F12 | 5.35 g/l | Asparagine | 40 mg/l |
| NaHCO$_3$ | 2.10 g/l | Serine | 80 mg/l |
| Glucose | 1.30 g/l | Ethanolamine | 3 mg/l |
| Lactose | 0.20 g/l | Glutamine | 0.20 g/l |
| Sodium Pyruvate | 0.11 g/l | Fetal Calf Serum | 100 ml/l |
| Glutamine | 1.90 g/l | Geneticin | 500 mg/l |

| Culture Medium no. 3 | | | |
|---|---|---|---|
| Basal Culture Medium + Insulin | | | |
| ISCOVE'S DMEM | 8.85 g/l | Tryptophan | 27 mg/l |
| HAM F12 | 5.35 g/l | Asparagine | 40 mg/l |
| NaHCO$_3$ | 2.10 g/l | Serine | 80 mg/l |
| Glucose | 1.30 g/l | Ethanolamine | 3 mg/l |
| Lactose | 0.20 g/l | Glutamine | 0.20 mg/l |
| Galactose | 0.20 g/l | Sodium Pyruvate | 0.11 g/l |
| Glutamine | 1.90 g/l | Insulin | 10 mg/l |

| HANK's Solution | | | |
|---|---|---|---|
| CaCl$_2 \cdot$ 2H$_2$O | 185 mg/l | Glucose | 1.0 g/l |
| MgSO$_4 \cdot$ 7H$_2$O | 140 mg/l | NaHCO$_3$ | 350 mg/l |
| KCl | 400 mg/l | KH$_2$PO$_4$ | 60 mg/l |
| NaCl | 8.0 g/l | Na$_2$HPO$_4$ | 47.8 mg/l |

What is claimed is:

1. A method for obtaining human erythropoietin comprising:
   (a) culturing and expanding mammalian cells selected from the group consisting of CHO, COS, BHK, Namalwa, and HeLa cells which express recombinant human erythropoietin in culture medium comprising serum;
   (b) culturing said cells of step (a) in culture medium consisting of:
      (i) DMEM (Dulbecco's modified Eagle's medium);
      (ii) F12 medium;
      (iii) insulin; and
      (iv) NaHCO$_3$, glucose, lactose, galactose, ethanolamine, pyruvate, glutamine, tryptophan, asparagine, and serine as additives;
   (c) separating supernatant containing human erythropoietin from said cells of step (b); and
   (d) concentrating said supernatant and recovering human erythropoietin from said supernatant.

2. The method of claim 1, wherein said mammalian cells comprise CHO cells.

3. The method of claim 1, wherein said culture medium of step (b) comprises greater than about 1 mg insulin per liter of culture medium.

4. The method of claim 1, wherein said culture medium of step (b) comprises less than about 20 mg insulin per liter of culture medium.

5. The method of claim 1, wherein said obtaining recovering comprises
   freezing the concentrated supernatant.

6. The method of claim 5, wherein said recovering further comprises sterile filtering the concentrated supernatant through membranes with pores of diameters of about 0.2 μm.

7. The method of claim 1, wherein said culture medium of step (b) is added to said separated cells of step (c) and said cells are cultured.

8. The method of claim 1, wherein said supernatant is concentrated from about 50 to 150 fold.

9. The method of claim 1, wherein said supernatant is concentrated about 100 fold.

10. The method of claim 1, wherein said concentrating comprises using a tangential filtration system through membranes with a molecular weight cut-off of about 3,000 Daltons.

11. The method of claim 1, wherein said culture medium of step (b) comprises about 10 mg insulin per liter of culture medium.

12. The method of claim 1, wherein said pyruvate is sodium pyruvate.

13. The method of claim 1, wherein said DMEM is Iscove's DMEM and wherein said F12 medium is HAM's F12 medium.

* * * * *

UNITED STATES PATENT AND TRADEMARK OFFICE
CERTIFICATE OF CORRECTION

PATENT NO. : 7,638,296 B1  Page 1 of 1
APPLICATION NO. : 09/830968
DATED : December 29, 2009
INVENTOR(S) : Carcagno et al.

It is certified that error appears in the above-identified patent and that said Letters Patent is hereby corrected as shown below:

On the cover page, section (56) Other Publications, line 4, please delete "Procucts and Referecnce" and insert therein -- Products and Reference --.

In column 10, line 48, claim 5, please delete "obtaining".

Signed and Sealed this

Sixteenth Day of March, 2010

David J. Kappos
*Director of the United States Patent and Trademark Office*

SEQUENCE LISTING

<160> NUMBER OF SEQ ID NOS: 1

<210> SEQ ID NO 1
<211> LENGTH: 165
<212> TYPE: PRT
<213> ORGANISM: Homo sapiens

<400> SEQUENCE: 1

Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
                20                  25                  30

Cys Ser Leu Asn Glu Asn Ile Thr Val Pro Asp Thr Lys Val Asn Phe
            35                  40                  45

Tyr Ala Trp Lys Arg Met Glu Val Gly Gln Gln Ala Val Glu Val Trp
        50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp
                165